US008142518B2

(12) United States Patent
Deconinck et al.

(10) Patent No.: US 8,142,518 B2
(45) Date of Patent: Mar. 27, 2012

(54) AGENT FOR DYEING AND/OR BLEACHING KERATIN FIBERS IN TWO PARTS, COMPRISING AT LEAST ONE FATTY SUBSTANCE AND AT LEAST ONE SEQUESTRANT

(75) Inventors: Gautier Deconinck, Saint-Gratien (FR); Caroline Goget, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/976,173

(22) Filed: Dec. 22, 2010

(65) Prior Publication Data

US 2011/0155167 A1   Jun. 30, 2011

Related U.S. Application Data

(60) Provisional application No. 61/297,420, filed on Jan. 22, 2010.

(30) Foreign Application Priority Data

Dec. 22, 2009   (FR) ..................................... 09 59433

(51) Int. Cl.
*A61Q 5/10* (2006.01)
(52) U.S. Cl. ............. 8/405; 8/406; 8/410; 8/431; 8/435; 8/455; 8/602; 8/604
(58) Field of Classification Search .............. 8/405, 406, 8/410, 431, 435, 455, 602, 604
See application file for complete search history.

(56) References Cited

U.S. PATENT DOCUMENTS

| | | | |
|---|---|---|---|
| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,826,681 A | 5/1989 | Jacquet et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |

(Continued)

FOREIGN PATENT DOCUMENTS

CA    1 268 421    5/1990

(Continued)

OTHER PUBLICATIONS

STIC Search Report dated May 13, 2011.*
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.

(Continued)

*Primary Examiner* — Eisa Elhilo
(74) *Attorney, Agent, or Firm* — Finnegan, Henderson, Farabow, Garrett & Dunner, LLP

(57) ABSTRACT

The present disclosure relates to an agent for dyeing and/or bleaching keratin fibers formed by: a first composition (A) comprising at least one basifying agent, and a second composition (B) comprising at least one oxidizing agent, wherein at least one of the two compositions (A) and (B) comprises at least one fatty substance not containing any carboxylic acid functional groups, the total amount of fatty substances in the mixture of compositions (A) and (B) representing at least 20% by weight relative to the total weight of the mixture of these compositions, and at least one of the compositions (A) and (B) comprises at least one sequestrant chosen from those of formula (I) and acids thereof:

$$\begin{array}{c} R_3 \\ \diagdown \\ N-(CH_2)_n-(Y)_p-(CH_2)_m-N \\ \diagup \\ R_4 \end{array} \begin{array}{c} R_1 \\ \diagup \\ \\ \diagdown \\ R_2 \end{array} \quad (I)$$

The present disclosure also relates to a process for dyeing and/or bleaching keratin fibers using the agent, and to a kit containing thereof.

24 Claims, No Drawings

U.S. PATENT DOCUMENTS

| | | | |
|---|---|---|---|
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,740,663 B2 | 6/2010 | De La Mettrie et al. |
| 7,766,977 B2 | 8/2010 | Cottard et al. |
| 7,799,095 B2 | 9/2010 | Mario et al. |
| 2002/0189034 A1 | 12/2002 | Kitabata et al. |
| 2003/0064494 A1 | 4/2003 | Kumar et al. |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0172771 A1* | 9/2004 | Cottard et al. | 8/405 |
| 2004/0181883 A1 | 9/2004 | Legrand et al. |
| 2004/0221400 A1 | 11/2004 | Cotteret et al. |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |
| 2010/0162492 A1 | 7/2010 | Hercouet et al. |
| 2010/0175705 A1 | 7/2010 | Hercouet et al. |
| 2010/0186177 A1 | 7/2010 | Hercouet et al. |
| 2010/0199441 A1 | 8/2010 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 198 42 071 | 3/2000 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 | 4/2009 |
| EP | 2 072 034 | 6/2009 |
| EP | 2 072 035 | 6/2009 |
| EP | 2 072 036 | 6/2009 |
| EP | 2 198 842 | 6/2010 |
| EP | 2 198 843 | 6/2010 |
| EP | 2 198 849 | 6/2010 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| FR | 2 940 054 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |

| | | |
|---|---|---|
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,093, filed Dec. 22, 2010.
Copending U.S. Appl. No. 12/976,124, filed Dec. 22, 2010.
Copending U.S. Appl. No. 12/976,150, filed Dec. 22, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 198 42 071, Mar. 16, 2000.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
European Search Report for EP 10 19 5262, dated Apr. 1, 2011.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.

French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
French Search Report for FR 09/59433, dated Sep. 24, 2010.
French Search Report for FR 09/59434, dated Sep. 24, 2010.
International Search Report for PCT/FR2009/052617, dated Mar. 30, 2010.
LookChem, poly[(dimethyliminio)-1,1,6-hexanediylchloride (1:2)], pp. 1-2, accesses Mar. 7, 2011.
Notice of Allowance mailed Apr. 1, 2011, in U.S. Appl. No. 12/642,506.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed in co-pending U.S. Appl. No. 12/642,468, dated Sep. 7, 2011.
Notice of Allowance mailed in co-pending U.S. Appl. No. 12/976,093, dated Oct. 5, 2011.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Mar. 9, 2011, in U.S. Appl. No. 12/642,473.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Jun. 8, 2011, in co-pending U.S. Appl. No. 12/339,781.
Office Action mailed Mar. 15, 2010, in co-pending U.S. Appl. No. 12/339,820.
Office Action mailed Mar. 16, 2011, in co-pending U.S. Appl. No. 12/642,583.
Office Action mailed Mar. 29, 2011, in co-pending U.S. Appl. No. 12/642468.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
P.R. Canterbery et al., International Cosmetic Ingredient Dictionary and Handbook, vol. 1, p. 759 (2002).
STIC Search Report for U.S. Appl. No. 12/339,820, dated Jan. 21, 2010.
STIC Search Report for U.S. Appl. No. 12/642,492, dated Jul. 14, 2010.
Ullmann's Encyclopedia of Industrial Chemistry, "Hair Preparations," Wiley-VCH Verlag GnbH & Co., KGaA, Weinheim, p. 20 (2006).

* cited by examiner

AGENT FOR DYEING AND/OR BLEACHING KERATIN FIBERS IN TWO PARTS, COMPRISING AT LEAST ONE FATTY SUBSTANCE AND AT LEAST ONE SEQUESTRANT

This application claims benefit of U.S. Provisional Application No. 61/297,420, filed Jan. 22, 2010. This application also claims benefit of priority under 35 U.S.C. §119 to French Patent Application No. 0959433, filed Dec. 22, 2009.

The present disclosure relates to an agent in two parts, for dyeing and/or bleaching keratin fibers, including human keratin fibers such as the hair.

For example, one aspect of the present disclosure is an agent for dyeing and/or bleaching keratin fibers, formed from a first composition (A) containing at least one basifying agent and optionally at least one dye, and a second composition (B) containing at least one oxidizing agent, at least one of the compositions (A) and (B) comprising at least one fatty substance not containing any carboxylic acid functional groups, and at least one specific sequestrant.

The present disclosure also relates to a multi-compartment device or kit containing the dyeing and/or bleaching agent according to the disclosure.

Furthermore, another aspect of the present disclosure is a process for dyeing and/or bleaching keratin fibers, using the agent according to the disclosure.

Many people have for a long time sought to modify the color of their hair, for example, to bleach it or, on the contrary, to dye it in order, for example, to mask their grey hair.

Two types of dyeing have been developed for dyeing keratin fibers.

The first type of dyeing is "permanent" or oxidation dyeing, which uses dye compositions containing oxidation dye precursors, generally known as oxidation bases. These oxidation bases are colorless or weakly colored compounds, which, when combined with oxidizing products, can give rise to colored compounds via a process of oxidative condensation.

It is also known that the shades obtained with these oxidation bases can be varied by combining them with couplers or coloration modifiers. The variety of molecules used as oxidation bases and couplers can allow a wide range of colors to be obtained.

The second type of dyeing is "semi-permanent" dyeing or direct dyeing. The process includes applying to keratin fibers direct dyes, which are colored and coloring molecules having affinity to the fibers, leaving them on for a period of time, and then rinsing said dyes off.

In order to perform these colorations, the direct dyes generally used are chosen from nitrobenzene, anthraquinone, nitropyridine, azo, xanthene, acridine, azine and triarylmethane direct dyes.

This type of process does not require the use of an oxidizing agent to develop the coloration. However, it is possible to use such an agent in order to obtain a lightening effect with the coloration. This is then referred to as direct or semi-permanent dyeing under lightening conditions.

Permanent or semi-permanent dyeing processes under lightening conditions using the dye composition usually include, an aqueous composition comprising at least one oxidizing agent, under alkaline pH conditions.

The conventional processes for bleaching human keratin fibers include using an aqueous composition comprising at least one oxidizing agent under generally alkaline pH conditions. The role of this oxidizing agent is to degrade the melanin of the hair, which can lead to more or less pronounced lightening of the fibers, depending on the nature of the oxidizing agent present. For relatively mild lightening, the oxidizing agent can be hydrogen peroxide. When greater lightening is desired, peroxygenated salts, for instance persulfates, can be used in the presence of hydrogen peroxide.

One of the difficulties encountered during the use of the dyeing and bleaching processes in the art can arise from the fact that they are performed under alkaline conditions.

In order to improve the performance qualities of processes for dyeing and/or bleaching human keratin fibers, and to limit the drawbacks associated with the use of alkaline agents and oxidizing agents, it has been proposed to use in dye compositions a substantial amount of at least one fatty substance.

However, during the process of mixing a composition comprising an alkaline agent and a composition comprising an oxidizing agent, both enriched in fatty substance, the resulting mixture can swell due to the evolution of oxygen.

This is inconvenient when the mixing of the components is performed just before application to the fibers: the gradual swelling of the mixture over time hampers its application to the fibers, and may make its application less precise. It may also cause poor homogeneity of the dyeing and/or bleaching.

Applicant has discovered that the use of certain sequestrants can reduce this swelling phenomenon, and can produce a mixture that remains almost unchanged over time, including during its application to keratin fibers.

One aspect of the present disclosure is thus an agent for dyeing and/or bleaching keratin fibers, consisting of:
a first composition (A) comprising at least one basifying agent, and
a second composition (B) comprising at least one oxidizing agent,
at least one of the two compositions (A) and (B) comprising at least one fatty substance not containing any carboxylic acid functional groups, the total amount of the at least one fatty substance in the mixture of compositions (A) and (B) representing at least 20% by weight relative to the total weight of the mixture, and
at least one of the compositions (A) and (B) comprising at least one sequestrant of formula (I):

$$\begin{array}{c} R_3 \\ \diagdown \\ N-(CH_2)_n-(Y)_p-(CH_2)_m-N \\ \diagup \\ R_4 \end{array} \begin{array}{c} R_1 \\ \diagup \\ \diagdown \\ R_2 \end{array} \qquad (I)$$

wherein
p is an integer equal to 0 or 1,
n and m are integers, independently of each other, equal to 0, 1 or 2, the sum n+m being equal to at least 1,
$R_1, R_2, R_3$ and $R_4$ represent, independently of each other, a hydrogen atom, $-CH_2CO_2M1$ or $-CH(CO_2M2)(CH_2CO_2M3)$,
Y represents $NCH_2CO_2M4$,
M1, M2, M3, and M4 denoting, independently of each other, a hydrogen atom, cations derived from an alkali metal or an alkaline-earth metal, cations derived from an optionally hydroxylated organic amine, or an ammonium cation,
with the understanding that if p is 0, then $R_1$ and $R_3$ both represent a hydrogen atom, and $R_2$ and $R_4$ both represent, independently of each other, $CH(CO_2M2)(CH_2CO_2M3)$, and
if p is 1, then n and m are each at least 1.

When the agent according to the disclosure is intended for dyeing keratin fibers, composition (A) also comprises at least one oxidation dye and/or at least one direct dye.

When the agent according to the disclosure is intended solely for bleaching keratin fibers, compositions (A) and (B) do not comprise any direct dyes or any oxidation dyes (bases and couplers), or if any direct dyes or oxidation dyes are present, their total content does not exceed 0.005% by weight relative to the weight of each composition. At such a content, only the composition would be dyed, i.e. no coloring effect would be observed on the keratin fibers.

The dyeing and/or bleaching agent according to the present disclosure does not change or changes little over time during the mixing of the compositions (A) and (B), or during the sequential application of these two compositions to the keratin fibers. It thus demonstrates the ease of application, good efficacy, and the quality and homogeneity of the dyeing and/or bleaching.

In addition, when the agent according to the disclosure is intended for dyeing, it also may be efficient in at least one of the resulting dyeing capacity, the capacity of the chromaticity, and the selectivity of dyeing of the same fiber or between differently sensitized fibers.

When the agent according to the disclosure is intended for bleaching, it can demonstrate lightening capacity greater than or equivalent to those obtained with the existing compositions, for example, those based on ammonium hydroxide.

The agent according to the disclosure may also have the benefit of limiting the aggressive odors during the preparation thereof or the application thereof to the fibers.

Other characteristics and benefits of the disclosure will emerge more clearly on reading the description and the examples that follow.

In the text hereinbelow, and unless otherwise indicated, the limits of a range of values are included in that range.

The human keratin fibers treated via the process according to the disclosure are, for example, hair.

According to the present disclosure, composition (A) comprises at least one basifying agent.

For the purposes of the disclosure, the term "basifying agent" means any compound which, via its presence in composition (A), increases the pH of this composition by at least 0.05 pH unit, such as at least 0.1 pH unit.

The basifying agent can be, for example, be a mineral or organic base.

For example, the basifying agent can be chosen from aqueous ammonia, alkali metal carbonates, alkanolamines and derivatives thereof, sodium hydroxide, potassium hydroxide and the compounds of formula (II):

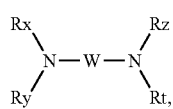

(II)

wherein W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of compounds of formula (II) that may be mentioned include, but are not limited to, 1,3-diaminopropane, 1,3-diamino-2-propanol, spermine and spermidine.

The basifying agents can be alkanolamines, for example, monoethanolamine, diethanolamine and triethanolamine, such as monoethanolamine.

In at least one embodiment, composition (A) comprises a basifying agent chosen from at least one organic amine, such as at least one alkanolamine. In at least one embodiment, composition (A) contains several basifying agents, such as an alkanolamine and aqueous ammonia or a salt thereof, wherein the organic amine(s) are, for example, in weight majority relative to the amount of ammonia present in composition (A).

In at least one embodiment of the present disclosure, composition (A) does not contain any aqueous ammonia.

In at least one embodiment of the present disclosure, composition (A) comprises aqueous ammonia or a salt thereof, and at least one alkanolamine, wherein the weight amount of alkanolamine(s) in composition (A) is greater than the weight amount of ammonia in this same composition.

Composition (A) has a content of basifying agent(s) ranging from 0.1% to 40% by weight, for example, from 0.5% to 20% by weight relative to the weight of this composition.

For instance, in at least one embodiment composition (A) has a pH greater than or equal to 8, for example, a pH ranging from 8.5 to 11.5.

This pH may also be adjusted to the desired value by using, for example, in addition to the basifying agent, at least one acidifying agent.

Among the acidifying agents, examples include, but are not limited to mineral or organic acids, for instance hydrochloric acid, orthophosphoric acid or sulfuric acid, carboxylic acids, for instance acetic acid, tartaric acid, citric acid or lactic acid, and sulfonic acids.

According to the present disclosure, composition (B) comprises at least one oxidizing agent. The at least one oxidizing agent may be chosen from the oxidizing agents such as hydrogen peroxide, urea peroxide, alkali metal bromates or ferricyanides, and peroxygenated salts, for instance persulfates, perborates and percarbonates of alkali metals or alkaline-earth metals such as sodium, potassium or magnesium. At least one redox enzyme such as laccases, peroxidases and 2-electron oxidoreductases (such as uricase), optionally in the presence of the respective donor or cofactor thereof, may also be used as oxidizing agent.

For example, the at least one oxidizing agent can be hydrogen peroxide. It may be for example, used as an aqueous solution (aqueous hydrogen peroxide solution) of which the concentration may vary from 0.1% to 50% by weight, for example, from 0.5% to 20% by weight, such as from 1% to 15% by weight relative to the total weight of composition (B).

Depending on the desired degree of bleaching, the oxidizing agent may also comprise at least one compound, such as peroxygenated salts.

For instance, in at least one embodiment, the pH of composition (B) is less than 7. This pH may be adjusted to the desired value by using at least one acidifying agent, which may be chosen from those described previously.

According to the present disclosure, one and/or the other of compositions (A) and (B) comprise at least one sequestrant of formula (I) as defined above.

In formula (I) above, M1, M2, M3 and M4 denote, independently of each other, a hydrogen atom, a cation derived from an alkali metal or from an alkaline-earth metal, a cation derived from an optionally hydroxylated organic amine, or an ammonium cation.

Examples of alkali metal cations include, but are not limited to, sodium ($Na^+$) and potassium ($K^+$); Examples of alkaline-earth metal cations, include, but are not limited to, calcium ($Ca^{2+}$) and magnesium ($Mg^{2+}$).

Examples of the cations of organic amines include, but are not limited to, the cations of primary, secondary or tertiary amines, or alkanolamines.

The amines can contain at least one radical, which may be identical or different, of linear or branched $C_1$ to $C_{20}$ alkyl or hydroxyalkyl type. In at least one embodiment, M1, M2, M3 and M4 are identical, and denote a sodium cation or a potassium cation.

According to the present disclosure, the sequestrants are, for example, diethylenetriaminepentaacetic acid (DTPA) and salts thereof, ethylenediaminedisuccinic acid (EDDS) and salts thereof.

The salts of these two compounds are, for example, the salts of alkali metals, such as the sodium or potassium salts.

According to the present disclosure, the at least one sequestrant may be present in composition (A) or in composition (B), or in both these compositions.

In at least one embodiment, composition (A) comprises at least one sequestrant.

In at least one embodiment, the at least one sequestrant is present only in composition (A).

Whether it is present in one, the other or both compositions (A) and (B), the total amount of the at least one sequestrant of formula (I) in acid form in the mixture of these compositions ranges from 0.001% to 10% by weight, for example, from 0.01% to 5% by weight, such as from 0.05% to 1% by weight relative to the total weight of the mixture of the compositions (A) and (B). These weight percentages are expressed relative to the acid form of the compound(s) of formula (I).

At least one of the compositions (A) and (B) comprises at least one fatty substance not containing any carboxylic acid functional groups, the total amount of such fatty substances in the mixture of compositions (A) and (B) representing at least 20% by weight relative to the total weight of the mixture of these two compositions (A) and (B).

Thus, the at least one fatty substance not containing any carboxylic acid functional groups may be present in composition (A) or composition (B), or in both the compositions, provided that the total amount of the at least one fatty substance in the mixture of compositions (A) and (B) is at least equal to 20% by weight relative to the total weight of the mixture of the compositions (A) and (B).

For example, the total amount of the at least one fatty substance not containing any carboxylic acid functional groups in the mixture of compositions (A) and (B) represents at least 25% by weight, such as at least 30% by weight relative to the total weight of the mixture.

The total amount of fatty substances not containing any carboxylic acid functional groups in the mixture of compositions (A) and (B) is, for example, less than or equal to 90% by weight, such as less than or equal to 70% by weight relative to the total weight of the mixture of the compositions (A) and (B).

According to at least one embodiment, composition (A) comprises at least one fatty substance not containing any carboxylic acid functional groups.

In the present disclosure, the term "fatty substance" means an organic compound that is insoluble in water at ordinary temperature (25° C.) and at atmospheric pressure (760 mmHg), i.e. which has a weight solubility in water of less than 5%, for example, less than 1%, such as less than 0.1%. The fatty substances contain in their structure at least one sequence of at least two siloxane groups or a hydrocarbon-based chain comprising at least 6 carbon atoms. In addition, the fatty substances can be soluble in organic solvents under the same temperature and pressure conditions, for instance chloroform, ethanol, benzene, liquid petroleum jelly or decamethylcyclopentasiloxane.

In the context of the disclosure, the at least one fatty substance containing at least one terminal carboxylic acid functional group such as fatty acids, which exhibits a certain level of solubility in water, for example, in alkaline medium, are excluded. The term "fatty substance not containing any carboxylic acid functional groups" means a fatty substance not containing any groups —COOH or any groups —COO⁻.

According to the disclosure, the at least one fatty substance not containing any carboxylic acid functional groups are chosen from compounds that are liquid or pasty at room temperature and at atmospheric pressure, for example, liquid compounds.

The at least one fatty substance not containing any carboxylic acid functional groups are, for example, chosen from $C_6$-$C_{16}$ lower alkanes, non-silicone oils of mineral, plant, animal and synthetic origin, fatty alcohols, fatty acid esters, and non-silicone waxes and silicones.

For the purposes of the disclosure, the fatty alcohols and fatty acids contain, for example, at least one linear or branched, saturated or unsaturated hydrocarbon-based group containing 6 to 30 carbon atoms, which are optionally substituted with, for example, at least one hydroxyl group (for example, 1 to 4 hydroxyl group). If the fatty alcohols and fatty acids are unsaturated, these compounds may comprise one to three conjugated or non-conjugated carbon-carbon double bonds.

In regard to the $C_6$-$C_{16}$ lower alkanes, they are linear or branched, or possibly cyclic. Examples include, but are not limited to, hexane, dodecane and isoparaffins such as isohexadecane and isodecane.

As oils of mineral, plant, animal or synthetic origin that may be used in the composition of the disclosure, examples include, but are not limited to:

hydrocarbon-based oils of animal origin, such as perhydrosqualene;

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, containing more than 16 carbon atoms, such as liquid paraffins, petroleum jelly, liquid petroleum jelly, polydecenes, and hydrogenated polyisobutene such as PARLEAM®;

fluoro oils, for instance perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the disclosure are, for example, chosen from linear or branched, saturated or unsaturated alcohols containing from 8 to 30 carbon atoms. Examples include, but are not limited to, cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

In regard to the esters of a fatty acid and/or of a fatty alcohol, they can be different from the triglycerides mentioned above; for example, esters of saturated or unsaturated, linear or branched $C_1$-$C_{26}$ aliphatic mono- or polyacids, and of saturated or unsaturated, linear or branched $C_1$-$C_{26}$ aliphatic mono- or polyalcohols, wherein the total carbon number of the esters being greater than or equal to 10.

Among the monoesters, example include, but are not limited to, dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

For example, the esters include, but are not limited to, diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

For example, the esters can be ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate; hexyl laurate, 2-hexyldecyl laurate, isononyl isononanoate or cetyl octanoate.

The composition may also comprise, as fatty ester, sugar esters and diesters of $C_6$-$C_{30}$ and for example $C_{12}$-$C_{22}$ fatty acids. The term "sugar" means oxygen-bearing hydrocarbon-based compounds containing several alcohol functional groups, with or without aldehyde or ketone functional groups, and which contain at least 4 carbon atoms. These sugars may be monosaccharides, oligosaccharides or polysaccharides.

Examples of suitable sugars include, but are not limited to, sucrose (or saccharose), glucose, galactose, ribose, fructose, maltose, mannose, arabinose, xylose and lactose, and derivatives thereof, for example, alkyl derivatives, such as methyl derivatives, for instance methylglucose.

The sugar esters of fatty acids may be chosen from the group comprising the esters or mixtures of esters of sugars described previously and of linear or branched, saturated or unsaturated $C_6$-$C_{30}$ and for example $C_{12}$-$C_{22}$ fatty acids. If they are unsaturated, these compounds may comprise one to three conjugated or non-conjugated carbon-carbon double bonds.

In at least one embodiment, the esters may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, oleopalmitate, oleostearate and palmitostearate mixed esters.

For example, monoesters and diesters, for example, sucrose, glucose or methylglucose mono- or dioleates, stearates, behenates, oleopalmitates, linoleates, linolenates and oleostearates.

The product sold under the name GLUCATE® by the company Amerchol is a methylglucose dioleate.

Examples of esters or mixtures of esters of sugar and of fatty acid include, but are not limited to:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name RYOTO SUGAR ESTER, for example referenced B370 and corresponding to sucrose behenate formed from 20% monoester and 80% di-triester-polyester;
the sucrose monodipalmitostearate sold by the company Goldschmidt under the name TEGOSOFT® PSE.

The non-silicone wax(es) are chosen from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant sold by the company Bertin (France), animal waxes, for instance beeswaxes, or modified beeswaxes (cerabellina); other waxes or waxy raw materials that may be used according to the disclosure are, for example, marine waxes such as the product sold by the company Sophim under the reference M82, and waxes of polyethylene or of polyolefins in general.

The silicones that may be used as fatty substances are volatile or non-volatile, cyclic, linear or branched silicones, which are unmodified or modified with organic groups, having a viscosity from $5\times10^{-6}$ to $2.5$ m$^2$/s at 25° C., for example, from $1\times10^{-5}$ to $1$ m$^2$/s.

The silicones that may be used in accordance with the disclosure may be in the form of oils, waxes, resins or gums.

For example, the silicone can be chosen from polydialkylsiloxanes, for example, polydimethylsiloxanes (PDMS), and organomodified polysiloxanes comprising at least one functional group chosen from poly(oxyalkylene) groups, amino groups and alkoxy groups.

The organopolysiloxanes are described in Walter Noll's *Chemistry and Technology of Silicones* (1968) Academic Press. They can be volatile or non-volatile.

When they are volatile, the silicones are, for example, chosen from those having a boiling point ranging from 60° C. to 260° C., for example:

(i) cyclic polydialkylsiloxanes containing from 3 to 7 and such as 4 to 5 silicon atoms. These are, for example, octamethylcyclotetrasiloxane sold, for example, under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Examples of cyclocopolymers of the dimethylsiloxane/methylalkylsiloxane type include, but are not limited to, VOLATILE SILICONE® FZ 3109 sold by the company Union Carbide, of formula:

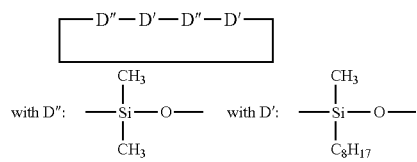

Examples of mixtures of cyclic polydialkylsiloxanes with organosilicon compounds include, but are not limited to, the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold, for example, under the name SH 200 by the company Toray Silicone. Silicones belonging to this category are also described in Todd & Byers "*Volatile Silicone Fluids for Cosmetics.*" Cosmetics and Toiletries, Vol. 91, January 76, pp. 27-32, For example, non-volatile polydialkylsiloxanes, polydialkylsiloxane gums and resins, polyorganosiloxanes modified with organofunctional groups above, and mixtures thereof, can be used.

These silicones are chosen from polydialkylsiloxanes, for example, polydimethylsiloxanes containing trimethylsilyl end groups. The viscosity of the silicones is measured, for example, at 25° C. according to ASTM standard 445 Appendix C.

Among these polydialkylsiloxanes, mention may be made, in a nonlimiting manner, of the following commercial products:

the SILBIONE® oils of the 47 and 70 047 series or the MIRASIL® oils sold by Rhodia, for instance the oil 70 047 V 500 000;
the oils of the MIRASIL® series sold by the company Rhodia;
the oils of the 200 series from the company Dow Corning, such as DC200 with a viscosity of 60,000 mm$^2$/s;
the VISCASIL® oils from General Electric and certain oils of the SF series (SF 96, SF 18) from General Electric.

For example, polydimethylsiloxanes containing dimethylsilanol end groups known under the name Dimethiconol (CTFA), such as the oils of the 48 series from the company Rhodia.

In this category of polydialkylsiloxanes, mention may also be made of the products sold under the names ABIL WAX® 9800 and 9801 by the company Goldschmidt, which are poly($C_1$-$C_{20}$)dialkylsiloxanes.

The silicone gums that can be used in accordance with the disclosure are, for example, polydialkylsiloxanes, such as polydimethylsiloxanes with high number-average molecular masses ranging from 200,000 to 1,000,000, or mixtures thereof in a solvent. This solvent can be chosen from volatile silicones, polydimethylsiloxane (PDMS) oils, poly-phenylmethylsiloxane (PPMS) oils, isoparaffins, polyisobutylenes, methylene chloride, pentane, dodecane and tridecane, or mixtures thereof.

Products that can be used in accordance with the disclosure are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;

mixtures of two PDMSs with different viscosities, for example, mixture of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. This product contains, for example 15% SE 30 gum and 85% SF 96 oil.

The organopolysiloxane resins that can be used in accordance with the disclosure are crosslinked siloxane systems containing the following units:

$R_2SiO_{2/2}, R_3SiO_{1/2}, RSiO_{3/2}$ and $SiO_{4/2}$ in which R represents an alkyl containing 1 to 16 carbon atoms, for example, a $C_1$-$C_4$ lower alkyl radical, such as methyl.

Among these resins, examples include, the product sold under the name Dow Corning 593 or those sold under the names Silicone Fluid SS 4230 and SS 4267 by the company General Electric, which are silicones of dimethyl/trimethyl siloxane structure.

Examples also include, but are not limited to, the trimethyl siloxysilicate type resins sold, for example, under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon-based group.

Besides the silicones described above, the organomodified silicones can be, but not limited to, polydiarylsiloxanes, for example, polydiphenylsiloxanes, and polyalkylarylsiloxanes functionalized with the organofunctional groups mentioned previously.

The polyalkylarylsiloxanes are chosen from linear and/or branched polydimethyl/methylphenylsiloxanes and polydimethyl/diphenylsiloxanes with a viscosity of from $1\times10^{-5}$ to $5\times10^{-2}$ m$^2$/s at 25° C.

For example, the products sold under the following names:
the SILBIONE® oils of the 70 641 series from Rhodia;
the oils of the RHODORSIL® 70 633 and 763 series from Rhodia;
the oil DOW CORNING 556 COSMETIC GRADE FLUID from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, examples of such include polyorganosiloxanes comprising:

substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups are, for example, $C_1$-$C_4$ aminoalkyl groups;

alkoxylated groups such as the product sold under the name Silicone Copolymer F-755 by SWS Silicones, and ABIL WAX® 2428, 2434 and 2440 by the company Goldschmidt.

For example, in at least one embodiment, the at least one fatty substance does not comprise any oxyalkylene units or any glycerolated units.

The at least one fatty substance not containing any carboxylic acid functional groups can be chosen, for example, from $C_6$-$C_{16}$ lower alkanes, non-silicone oils of mineral, plant or synthetic origin, fatty alcohols, fatty acid esters, fatty alcohol esters and silicones. For example, the at least one fatty substance of the composition according to the disclosure is non-silicone.

In at least one embodiment, the at least one fatty substance is chosen from liquid petroleum jelly, polydecenes, and liquid esters of fatty acids and liquid esters of fatty alcohols, for example, liquid petroleum jelly.

Compositions (A) and/or (B) according to the present disclosure may also comprise at least one surfactant.

The at least one surfactant can be chosen from, for example, nonionic surfactants and from anionic surfactants. The anionic surfactants can be chosen from the salts (for example, alkali metal salts, such as sodium salts, ammonium salts, amine salts, amino alcohol salts or alkaline-earth metal salts such as magnesium salts) of the following compounds:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefin sulfonates, paraffin sulfonates;

alkyl phosphates, alkyl ether phosphates;

alkylsulfosuccinates, alkyl ether sulfosuccinates, alkylamidesulfosuccinates; alkylsulfosuccinamates;

alkylsulfoacetates;

acylsarcosinates; acylisethionates and N-acyltaurates;

salts of fatty acids such as oleic acid, ricinoleic acid, palmitic acid or stearic acid, coconut oil acid or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, for example, those containing from 2 to 50 ethylene oxide groups;

and mixtures thereof.

The alkyl or acyl radical of these various compounds can contain from 6 to 24 carbon atoms, for example, from 8 to 24 carbon atoms, and the aryl radical denotes, for example, a phenyl or benzyl group.

The nonionic surfactants can be chosen from, for example, monooxyalkylenated or polyoxyalkylenated nonionic surfactants different from the abovementioned nonionic surfactants, or from monoglycerolated or polyglycerolated nonionic surfactants. The oxyalkylene units are, for example, oxyethylene or oxypropylene units, or a combination thereof, such as oxyethylene units.

Examples of oxyalkylenated nonionic surfactants that may be mentioned include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_{8-30}$ acids and of sorbitol, saturated or unsaturated, oxyethylenated plant oils, condensates of ethylene oxide and/or of propylene oxide, inter alia, and mixtures thereof.

These surfactants contain a number of moles of ethylene oxide and/or propylene oxide ranging from 1 to 100, for example, from 2 to 50. In at least one embodiment, the nonionic surfactants do not comprise any oxypropylene units.

In at least one embodiment of the disclosure, the oxyalkylenated nonionic surfactants are chosen from oxyethylenated $C_8$-$C_{30}$ alcohols, and polyoxyethylenated esters of saturated or unsaturated, linear or branched $C_8$-$C_{30}$ acids and of sorbitol.

Examples of monoglycerolated or polyglycerolated nonionic surfactants include, but are not limited to, monoglycerolated and polyglycerolated $C_8$-$C_{40}$ alcohols. For example, the monoglycerolated or polyglycerolated $C_8$-$C_{40}$ alcohols can be chosen from those of the following formula:

$$RO-[CH_2-CH(CH_2OH)-O]_m-H,$$

wherein R represents a linear or branched $C_8$-$C_{40}$, such as, $C_8$-$C_{30}$ alkyl or alkenyl radical, and m represents a number ranging from 1 to 30, such as from 1 to 10.

For example, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same respect that the value of m represents a statistical value. It means that, in a commercial product, several species of polyglycerolated fatty alcohol may coexist in the form of a mixture.

Non-limiting examples of the monoglycerolated or polyglycerolated alcohols are the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

In at least one embodiment, the agent comprises at least one nonionic surfactant. For example, composition (A) comprises at least one surfactant.

The surfactant(s) may be present in proportions ranging from 0.1% to 50% by weight, for example, from 0.5% to 30% by weight relative to the total weight of each composition in which they are contained.

Compositions (A) and/or (B) according to the present disclosure may also comprise at least one mineral thickener chosen from organophilic clays and fumed silicas, or mixtures thereof. The organophilic clay may be chosen from montmorillonite, bentonite, hectorite, attapulgite and sepiolite, and mixtures thereof, for example, a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof. Organophilic clays that may be mentioned, for example, include quaternium-18 bentonites such as those sold under the names BENTONE 3, BENTONE 38 and BENTONE 38V by the company Rheox, TIXOGEL VP by the company United Catalyst, CLAYTONE 34, CLAYTONE 40 and CLAYTONE XL by the company Southern Clay; stearalkonium bentonites such as those sold under the names BENTONE 27 by the company Rheox, TIXOGEL LG by the company United Catalyst and CLAYTONE AF and CLAYTONE APA by the company Southern Clay; quaternium-18/benzalkonium bentonites such as those sold under the names CLAYTONE HT and CLAYTONE PS by the company Southern Clay.

The fumed silicas may be obtained by high-temperature hydrolysis of a volatile silicon compound in an oxhydric flame, producing a finely divided silica. This process makes it possible to, for example, obtain hydrophilic silicas having a large number of silanol groups at their surface. Such hydrophilic silicas are sold, for example, under the names AEROSIL 130®, AEROSIL 200®, AEROSIL 255®, AEROSIL 300® and AEROSIL 380® by the company Degussa, and CAB-O-SIL HS-5®, CAB-O-SIL EH-5®, CAB-O-SIL LM-130®, CAB-O-SIL MS-55® and CAB-O-SIL M-5® by the company Cabot.

It is possible to chemically modify the surface of the said silica, via a chemical reaction generating a reduction in the number of silanol groups. For example, it is possible to substitute silanol groups with hydrophobic groups to obtain a hydrophobic silica.

The hydrophobic groups can be:
trimethylsiloxyl groups, which are obtained, for example, by treating fumed silica in the presence of hexamethyldisilazane. Silicas thus treated are known as "silica silylate" according to the CTFA (6th Edition, 1995). They are sold, for example, under the references AEROSIL R812® by the company Degussa and CAB-O-SIL TS-530® by the company Cabot;
dimethylsilyloxyl or polydimethylsiloxane groups, which are obtained, for example, by treating fumed silica in the presence of polydimethylsiloxane or dimethyldichlorosilane. Silicas thus treated are known as "silica dimethyl silylate" according to the CTFA (6th Edition, 1995). They are sold, for example, under the references AEROSIL R972® and AEROSIL R974® by the company Degussa and CAB-O-SILTS-610® and CAB-O-SILTS-720® by the company Cabot.

The fumed silica may have, for example a particle size that may be nanometric to micrometric, for example ranging from about 5 to 200 nm.

In at least one embodiment, the mineral thickeners are chosen from hectorites, organomodified bentonites and optionally modified fumed silicas.

When it is present, the mineral thickener represents from 1% to 30% by weight relative to the weight of the composition in which it is present.

Compositions (A) and/or (B) according to the present disclosure may also comprise at least one organic thickener.

These thickeners may be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

In at least one embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum) and acrylic acid or acrylamidopropanesulfonic acid crosslinked homopolymers, for example, cellulose-based thickeners such as hydroxyethylcellulose.

The content of organic thickener(s), if present, can range from 0.01% to 20% by weight, for example, from 0.1% to 5% by weight relative to the weight of each composition in which they are present.

In at least one embodiment, composition (A) is in the form of a gel or a cream.

In at least one embodiment, composition (B) is in the form of a solution, an emulsion or a gel.

In at least one embodiment of the disclosure, composition (A) also comprises at least one oxidation dye. In this case, the agent according to the disclosure can be used for the oxidation dyeing of keratin fibers. In at least one embodiment, composition (A) may also comprise at least one direct dye.

In at least one embodiment of the disclosure, composition (A) also comprises at least one direct dye.

In this case, and when composition (A) does not comprise any oxidation dyes, the agent according to the disclosure can be used for the lightening direct dyeing of keratin fibers.

The at least one oxidation dye that may be used in the present disclosure can be chosen from oxidation bases, optionally combined with at least one coupler.

The oxidation bases may be chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylene-diamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(3-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β- acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may be further mentioned.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diamino-phenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present disclosure are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-yl-pyrazolo[1,5-a]pyrid-3-ylamine, 2-[(3-aminopyrazolo[1,5-a]pyrid-5-yl)(2-hydroxy-ethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 2526099; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for example, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used, for example, In at least one embodiment, 4,5-diaminopyrazole, such as 4,5-diamino-1-(β-hydroxyethyl)pyrazole and/or a salt thereof is used.

Pyrazole derivatives that may also be mentioned include, but are not limited to, diamino-N,N-dihydropyrazolopyrazolones, for example, those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one. For example, 2,3-Diamino-6,7-dihydro-1H,5H-pyrazolo[1,2-a]pyrazol-1-one and/or a salt thereof may be used.

Examples of heterocyclic bases include, but are not limited to, 4,5-Diamino-1-(β-hydroxyethyl)pyrazole and/or 2,3-diamino-6,7-dihydro-1H,5H-pyrazolo[1,2-a]pyrazol-1-one and/or a salt thereof.

The couplers that may be used in the present disclosure may be chosen from those used for the dyeing of keratin fibers. For example, mention may be made of meta-phenylenediamines, meta-aminophenols, meta-diphenols, naphthalene-based couplers and heterocyclic couplers, and also the addition salts thereof. Example of such include, but are not limited to, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The addition salts of the oxidation bases and couplers that may be used in the context of the disclosure can be chosen from the addition salts with an acid such as the hydrochlorides, hydrobromides, sulfates, citrates, succinates, tartrates, lactates, tosylates, benzenesulfonates, phosphates and acetates.

The at least one oxidation base may each represent from 0.001% to 10% by weight relative to the total weight of composition (A), such as from 0.005% to 5% by weight relative to the total weight of this composition.

The at least one coupler, if present, may each represent from 0.001% to 10% by weight relative to the total weight of composition (A), such as from 0.005% to 5% by weight relative to the total weight of the agent.

The at least one direct dye that may be used in composition (A) can be chosen from ionic and nonionic species, such as cationic or nonionic species.

Examples of direct dyes suitable for use include, but are not limited to, azo, methine, carbonyl, azine, nitro (hetero)aryl; tri(hetero)arylmethane, porphyrin, phthalocyanin direct dyes, and natural direct dyes, or mixtures thereof.

For example, the azo dyes comprise an —N=N— function, the two nitrogen atoms of which are not simultaneously engaged in a ring. However, it is not excluded for one of the two nitrogen atoms of the sequence —N=N— to be engaged in a ring.

The dyes of the methine family can be compounds comprising at least one sequence chosen from >C=C< and —N=C<, the two atoms of which are not simultaneously engaged in a ring. However, one of the nitrogen or carbon atoms of the sequences may be engaged in a ring. For example, the dyes of this family are derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

In regard to the dyes of the carbonyl family, examples that may be mentioned include, but are not limited to, dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

In regard to the dyes of the cyclic azine family, non-limiting mention may be made of azine, xanthene, thioxanthene, fluorindine, acridine, (di)oxazine, (di)thiazine and pyronin.

In regard to the nitro (hetero)aromatic dyes, example include, but are not limited to, nitrobenzene or nitropyridine direct dyes.

In regard to the dyes of porphyrin or phthalocyanin type, examples include, but are not limited to, cationic or non-cationic compounds, optionally comprising at least one metal or metal ion, such as alkali metals, alkaline-earth metals, zinc and silicon.

Examples of suitable direct dyes include, but are not limited to, nitrobenzene dyes; azo direct dyes, azomethine direct dyes, methine direct dyes, azacarbocyanin direct dyes such as tetraazacarbocyanins (tetraazapentamethines), quinone such as anthraquinone, naphthoquinone or benzoquinone direct dyes, azine, xanthene, triarylmethane, indoamine, indigoid, phthalocyanin direct dyes, porphyrins and natural direct dyes, or mixtures thereof.

These dyes may be monochromophoric dyes (i.e. comprising only one dye) or polychromophoric such as di- or trichromophoric; the chromophores possibly being identical or different, and from the same chemical family or otherwise. A polychromophoric dye comprises several radicals each derived from a molecule that absorbs in the visible region between 400 and 800 nm. Furthermore, this absorbance of the dye does not require any prior oxidation thereof, or combination with any other chemical species.

In the case of polychromophoric dyes, the chromophores are connected together via at least one linker, which may be cationic or non-cationic.

In at least one embodiment, the linker is a linear, branched or cyclic $C_1$-$C_{20}$ alkyl chain, optionally interrupted with at least one heteroatom (such as nitrogen or oxygen) and/or with at least one group comprising such an atom (CO, $SO_2$), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

If the heterocycles or aromatic nuclei are substituted, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino, or amino group substituted with one or two $C_1$-$C_4$ alkyl radicals, optionally bearing at least one hydroxyl group, or the two radicals possibly forming, with the nitrogen atom to which they are attached, a 5- or 6-membered heterocycle optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals optionally bearing at least one hydroxyl group.

Among the benzenic direct dyes that may be used according to the disclosure, mention may be made in a nonlimiting manner of the following compounds:
1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene 1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine, methine and tetraazapentamethine direct dyes that may be used according to the disclosure, non-limiting mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

In at least one embodiment, dyes of formulae (I) to (IV), for example, the compounds of formulae (I) and (III), are used:

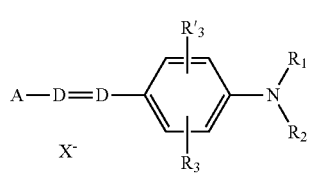

(I)

wherein,

D represents a nitrogen atom or a —CH group, $R_1$ and $R_2$, which may be identical or different, represent a hydrogen atom; a $C_1$-$C_4$ alkyl radical which may be substituted with a —CN, —OH or —NH$_2$ radical, or form, with a carbon atom of the benzene ring, a heterocycle optionally containing oxygen or nitrogen, which may be substituted with at least one $C_1$-$C_4$ alkyl radical; a 4'-aminophenyl radical, $R_3$ and $R'_3$, which may be identical or different, represent a hydrogen atom or a halogen atom chosen from chlorine, bromine, iodine and fluorine, or a cyano, $C_1$-$C_4$ alkyl, $C_1$-$C_4$ alkoxy or acetyloxy radical, $X^-$ represents an anion for example chosen from chloride, methyl sulfate and acetate, A represents a group chosen from structures A1 to A18, for example, A1, A4, A7, A13 and A18, below:

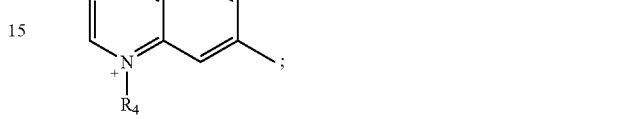

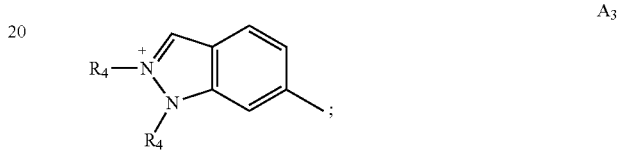

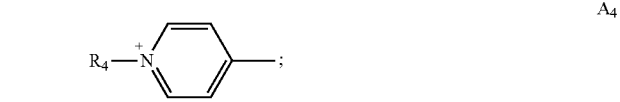

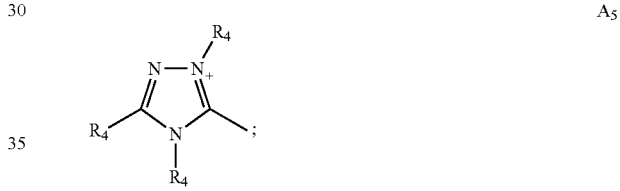

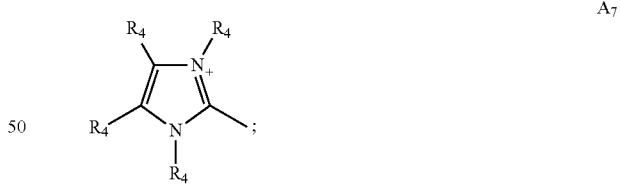

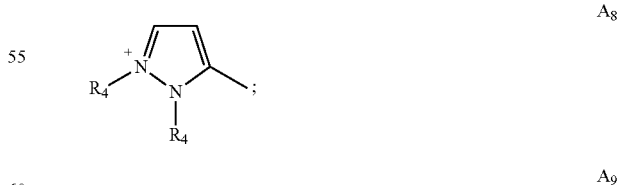

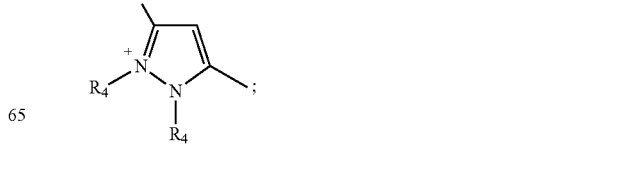

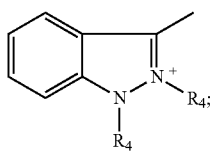 A₁₀

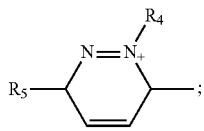 A₁₁

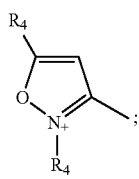 A₁₂

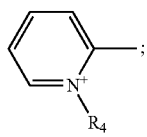 A₁₃

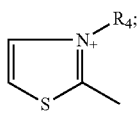 A₁₄

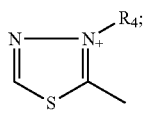 A₁₅

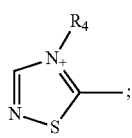 A₁₆

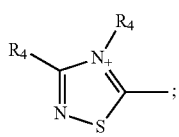 A₁₇

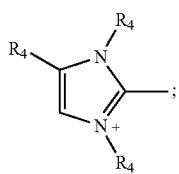 A₁₈ wherein $R_4$ represents a $C_1$-$C_4$ alkyl radical which may be substituted with a hydroxyl radical and $R_5$ represents a $C_1$-$C_4$ alkoxy radical;

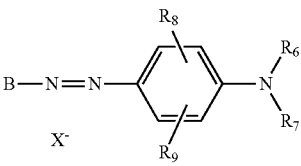 (II)

wherein:

$R_6$ represents a hydrogen atom or a $C_1$-$C_4$ alkyl radical, $R_7$ represents a hydrogen atom, an alkyl radical which may be substituted with a —CN radical or with an amino group, a 4'-aminophenyl radical, or forms with $R_6$ a heterocycle optionally containing oxygen and/or nitrogen, which may be substituted with a $C_1$-$C_4$ alkyl radical, $R_8$ and $R_9$, which may be identical or different, represent a hydrogen atom, a halogen atom such as bromine, chlorine, iodine or fluorine, a $C_1$-$C_4$ alkyl or $C_1$-$C_4$ alkoxy radical, or a —CN radical, $X^-$ represents an anion for example chosen from chloride, methyl sulfate and acetate, B represents a group chosen from structures B1 to B6 below:

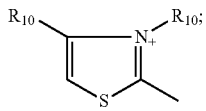 B1

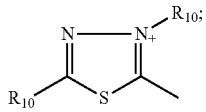 B2

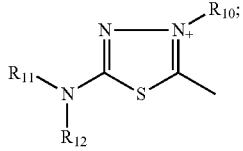 B3

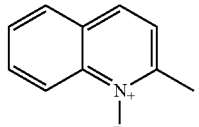 B4

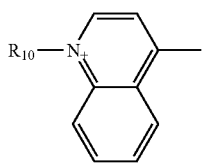 B5

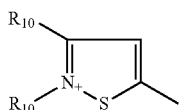 B6 wherein, $R_{10}$ represents a $C_1$-$C_4$ alkyl radical, $R_{11}$ and $R_{12}$, which may be identical or different, represent a hydrogen atom or a $C_1$-$C_4$ alkyl radical;

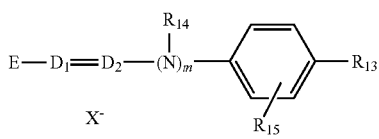
(III)

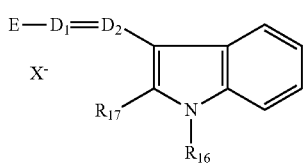
(III')

wherein, $R_{13}$ represents a hydrogen atom, a $C_1$-$C_4$ alkoxy radical, a halogen atom such as bromine, chlorine, iodine or fluorine, or an amino radical, $R_{14}$ represents a hydrogen atom, a $C_1$-$C_4$ alkyl radical or forms, with a carbon atom of the benzene ring, a heterocycle optionally containing oxygen and/or substituted with at least one $C_1$-$C_4$ alkyl group, $R_{15}$ represents a hydrogen atom or a halogen atom such as bromine, chlorine, iodine or fluorine, $R_{16}$ and $R_{17}$, which may be identical or different, represent a hydrogen atom or a $C_1$-$C_4$ alkyl radical, $D_1$ and $D_2$, which may be identical or different, represent a hydrogen atom or a —CH group, m=0 or 1, for example 1, with the understanding that when $R_{13}$ represents an unsubstituted amino group, then $D_1$ and $D_2$ simultaneously represent a —CH group and m=0, X⁻ represents an anion for example chosen from chloride, methyl sulfate and acetate, E represents a group chosen from structures E1 to E8, for example, E1, E2 and E7, below:

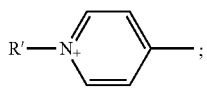
E1

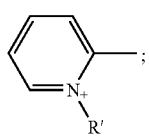
E2

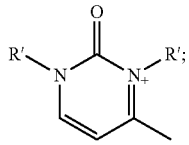
E3

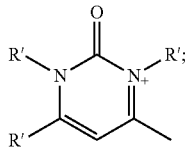
E4

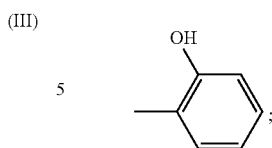
E5

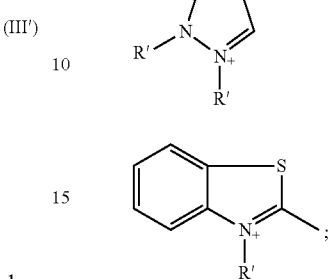
E6

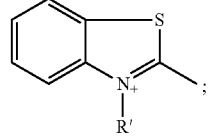
and

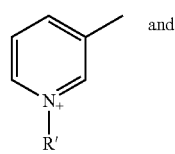
E7

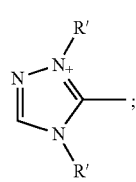
E8 in which R' represents a $C_1$-$C_4$ alkyl radical;

provided that, when m=0 and $D_1$ represents a nitrogen atom, then E may also denote a group of structure E9 below:

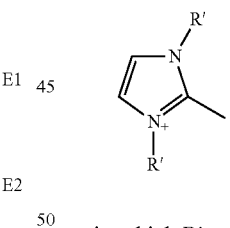
E9 in which R' represents a $C_1$-$C_4$ alkyl radical.

(IV)

wherein,

G represents a group chosen from the structures $G_1$ to $G_3$ below:

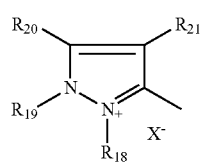
$G_1$

-continued

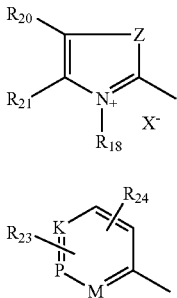

G₂

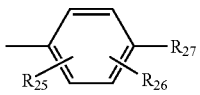

G₃ wherein, $R_{18}$ denotes a $C_1$-$C_4$ alkyl radical, a phenyl radical which may be substituted with a $C_1$-$C_4$ alkyl radical, or a halogen atom chosen from chlorine, bromine, iodine and fluorine;

$R_{19}$ denotes a $C_1$-$C_4$ alkyl radical or a phenyl radical;

$R_{20}$ and $R_{21}$, which may be identical or different, represent a $C_1$-$C_4$ alkyl radical, a phenyl radical, or form together in $G_1$ a benzene ring substituted with at least one $C_1$-$C_4$ alkyl, $C_1$-$C_4$ alkoxy or $NO_2$ radical, or form together in $G_2$ a benzene ring optionally substituted with at least one $C_1$-$C_4$ alkyl, $C_1$-$C_4$ alkoxy or $NO_2$ radical;

$R_{20}$ may also denote a hydrogen atom;

Z represents an oxygen or sulfur atom or a group —$NR_{19}$;

M represents a group —CH, —CR (R denoting $C_1$-$C_4$ alkyl) or —$NR_{22}(X^-)_r$;

K represents a group —CH, —CR (R denoting $C_1$-$C_4$ alkyl) or —$NR_{22}(X^-)_r$;

P represents a group —CH, —CR (R denoting $C_1$-$C_4$ alkyl) or —$NR_{22}(X^-)_r$;

r denotes 0 or 1;

$R_{22}$ represents an $O^-$ atom, a $C_1$-$C_4$ alkoxy radical or a $C_1$-$C_4$ alkyl radical;

$R_{23}$ and $R_{24}$, which may be identical or different, represent a hydrogen atom or a halogen atom chosen from chlorine, bromine, iodine and fluorine, a $C_1$-$C_4$ alkyl or $C_1$-$C_4$ alkoxy radical, or an —$NO_2$ radical;

$X^-$ represents an anion for example chosen from chloride, iodide, methyl sulfate, ethyl sulfate, acetate and perchlorate;

provided that, if $R_{22}$ denotes $O^-$, then r denotes zero;

if K or P or M denote —N—$(C_1$-$C_4)$alkyl $X^-$, then $R_{23}$ or $R_{24}$ is for example different than a hydrogen atom;

if K denotes —$NR_{22}(X^-)_r$, then M=P=—CH, —CR;

if M denotes —$NR_{22}(X^-)_r$, then K=P=—CH, —CR;

if P denotes —$NR_{22}(X^-)_r$, then K=M and denotes —CH or —CR;

if Z denotes a sulfur atom with $R_{21}$ denoting $C_1$-$C_4$ alkyl, then $R_{20}$ is other than a hydrogen atom;

if Z denotes —$NR_{22}$ with $R_{19}$ denoting $C_1$-$C_4$ alkyl, then at least one of the radicals $R_{18}$, $R_{20}$ or $R_{21}$ of the group of structure $G_2$ is other than a $C_1$-$C_4$ alkyl radical;

J represents:

(a) a group of structure $J_1$ below:

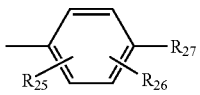

J₁ in which structure $J_1$:

$R_{25}$ represents a hydrogen atom, a halogen atom chosen from chlorine, bromine, iodine and fluorine, a $C_1$-$C_4$ alkyl or $C_1$-$C_4$ alkoxy radical, an —OH, —$NO_2$, —$NHR_{28}$, —$NR_{29}R_{30}$ or $C_1$-$C_4$—NHCOalkyl radical, or forms with $R_{26}$ a 5- or 6-membered ring optionally containing at least one heteroatom chosen from nitrogen, oxygen and sulfur;

$R_{26}$ represents a hydrogen atom, a halogen atom chosen from chlorine, bromine, iodine and fluorine, a $C_1$-$C_4$ alkyl or $C_1$-$C_4$ alkoxy radical, or forms with $R_{27}$ or $R_{28}$ a 5- or 6-membered ring optionally containing at least one heteroatom chosen from nitrogen, oxygen and sulfur;

$R_{27}$ represents a hydrogen atom, an —OH radical, a radical —$NHR_{28}$ or a radical —$NR_{29}R_{30}$;

$R_{28}$ represents a hydrogen atom, a $C_1$-$C_4$ alkyl radical, a $C_1$-$C_4$ monohydroxyalkyl, $C_2$-$C_4$ polyhydroxyalkyl radical or a phenyl radical;

$R_{29}$ and $R_{30}$, which may be identical or different, represent a $C_1$-$C_4$ alkyl radical, a $C_1$-$C_4$ monohydroxyalkyl or $C_2$-$C_4$ polyhydroxyalkyl radical;

(b) a 5- or 6-membered nitrogenous heterocyclic group, which may contain other heteroatoms and/or carbonyl groups and may be substituted with at least one $C_1$-$C_4$ alkyl, amino or phenyl radical, for example, a group of structure $J_2$ below:

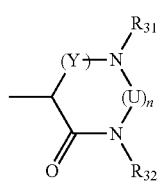

J₂ wherein structure $J_2$:

$R_{31}$ and $R_{32}$, which may be identical or different, represent a hydrogen atom, a $C_1$-$C_4$ alkyl radical or a phenyl radical;

Y denotes a —CO— radical or a

radical;

n=0 or 1, with, when n denotes 1, U denoting a —CO— radical.

In at least one embodiment, the structures of dyes (I) to (IV) defined above, are such that the $C_1$-$C_4$ alkyl or alkoxy group denotes methyl, ethyl, butyl, methoxy or ethoxy.

Among the compounds of formulae (I) and (III) mention may be made of:

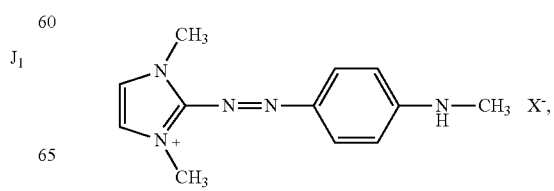

-continued

[Chemical structures with X⁻ counterions showing imidazolium-azo-aniline derivatives and pyridinium-hydrazone compounds]

Among the azo direct dyes that may also be mentioned are the following dyes described in the Color Index International, 3rd edition:
Disperse Red 17
Basic Red 22
Basic Red 76
Basic Yellow 57
Basic Brown 16
Basic Brown 17
Disperse Black 9.

In at least one embodiment, the disclosure is directed to 1-(4'-amino-diphenylazo)-2-methyl-4-bis(β-hydroxyethyl) aminobenzene.

Examples of the quinone direct dyes include, but are not limited to:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
and the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Examples of azine dyes include, but are not limited to, the following compounds:
Basic Blue 17
Basic Red 2.

Examples of triarylmethane dyes include, but are not limited to, the following compounds:
Basic Green 1
Basic Violet 3
Basic Violet 14
Basic Blue 7
Basic Blue 26.

Examples of indoamine dyes include, but are not limited to, the following compounds:
2-β-hydroxyethylamino-5-[bis(β-4'-hydroxyethyl)amino] anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenylureido-6-methyl-1,4-benzoquinone imine.

Examples of dyes of tetraazapentamethine type include, but are not limited to, the compounds in the table below:

[Chemical structures of tetraazapentamethine dyes with X⁻ counterions, featuring bis-imidazole, bis-methoxypyridine, and bis-pyridine bridged azomethine systems]

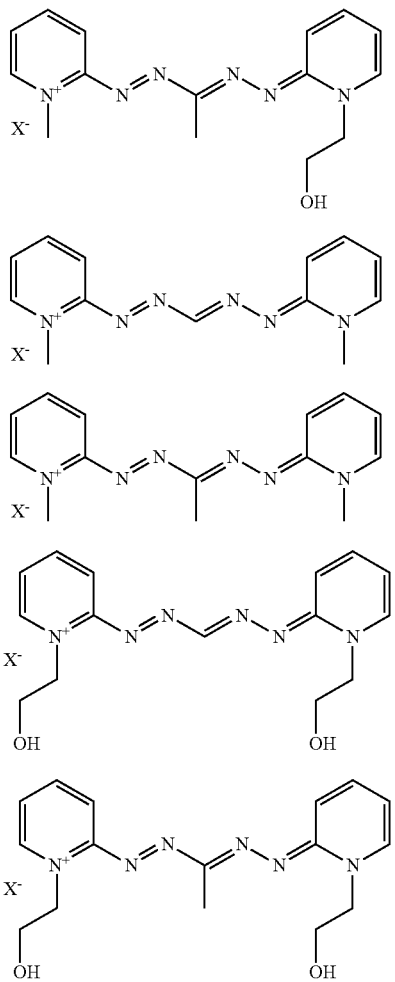

wherein X⁻ represents an anion for example chosen from chloride, iodide, methyl sulfate, ethyl sulfate, acetate and perchlorate.

Examples of polychromophoric dyes include, but are not limited to, symmetrical or non-symmetrical azo and/or azomethine (hydrazone) di- or trichromophoric dyes comprising, (I) at least one optionally fused 5- or 6-membered aromatic heterocycle, comprising at least one quaternized nitrogen atom engaged in said heterocycle and optionally at least one other heteroatom (such as nitrogen, sulfur or oxygen), and, (II) at least one optionally substituted phenyl or naphthyl group, optionally bearing at least one group OR with R representing a hydrogen atom, an optionally substituted $C_1$-$C_6$ alkyl radical, an optionally substituted phenyl nucleus, or at least one group N(R')$_2$ with R', which may be identical or different, representing a hydrogen atom, an optionally substituted $C_1$-$C_6$ alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Examples of aromatic cationic heterocycles include, but are not limited to, 5- or 6-membered rings containing 1 to 3 nitrogen atoms such as 1 or 2 nitrogen atoms, one being quaternized; said heterocycle moreover being optionally fused to a benzene nucleus. The heterocycle may optionally comprise another heteroatom other than nitrogen, for instance sulfur or oxygen.

If the heterocycles or phenyl or naphthyl groups are substituted, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino or amino group substituted with one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals, optionally bearing at least one hydroxyl group.

These polychromophores can be connected together via at least one linker optionally comprising at least one quaternized nitrogen atom that may or may not be engaged in a saturated or unsaturated, optionally aromatic heterocycle.

For instance, the linker can be a linear, branched or cyclic $C_1$-$C_{20}$ alkyl chain, optionally interrupted with at least one heteroatom (such as nitrogen or oxygen) and/or with at least one group comprising such a heteroatom (CO or SO$_2$), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

The bonding between the linker and each chromophore can take place via a heteroatom substituent on the phenyl or naphthyl nucleus or via the quaternized nitrogen atom of the cationic heterocycle.

The dye may comprise identical or different chromophores.

As examples of such dyes, non-limiting reference may be made to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

It is also possible to use the cationic direct dyes mentioned in patent applications: EP 1 006 153, which describes dyes comprising two chromophores of anthraquinone type connected via a linker of cationic type; EP 1 433 472, EP 1 433 474, EP 1 433 471 and EP 1 433 473, which describe identical or different dichromophoric dyes, connected via a cationic or non-cationic linker, and EP 6 291 333, which describes dyes comprising three chromophores, one of them being an anthraquinone chromophore, to which are attached two chromophores of azo or diazacarbocyanin type or an isomer thereof.

Examples of natural direct dyes that may be used according to the disclosure include, but are not limited to, lawsone, juglone, alizarin, purpurin, carminic acid, kermesic acid, purpurogallin, protocatechaldehyde, indigo, isatin, curcumin, spinulosin, apigenidin and orceins. It is also possible to use extracts or decoctions containing these natural dyes, such as henna-based poultices or extracts.

When they are present, the direct dye(s) represent from 0.001% to 10% by weight, for example, from 0.005% to 5% by weight relative to the total weight of composition (A).

In at least one embodiment of the disclosure, compositions (A) and (B) do not comprise any direct dyes or any oxidation dyes (bases and couplers), or if the direct dyes or oxidation dyes are present, their total content does not exceed 0.005% by weight relative to the total weight of each composition.

In at least one embodiment, the agent according to the disclosure is used for bleaching keratin fibers.

In at least one embodiment, composition (A) may comprise at least one solid or pasty adjuvant, which is pulverulent. The adjuvant may then be chosen from clays, salts other than ammonium salts, anionic, nonionic, cationic or zwitterionic surfactants, natural or synthetic thickeners, optionally modified starch, glass beads, silica, Nylon, alumina, titanium dioxide, zeolites, poly(methyl methacrylate) (PMMA), chitosan, maltodextrin, cyclodextrin, monosaccharides or disaccharides, for instance glucose, sucrose, sorbitol or fructose, zinc oxide, zirconium oxide, silica beads, talc, borosilicates, for example, of calcium, polyethylene, polytetrafluoroethylene (PTFE), cellulose and derivatives thereof, superabsorbent compounds, magnesium or calcium carbonates, polyacrylamide, porous hydroxyapatite, sawdust, fucus powder, crosslinked polyvinylpyrrolidone, calcium alginate, active charcoal, poly(vinylidene chloride/acrylonitrile) particles, for example, those sold under the general name EXPANCEL® by the company Akzo Nobel under the particular references EXPANCEL® WE or DE, and mixtures thereof.

In at least one embodiment, compositions (A) and (B) are formulated in a cosmetically acceptable medium comprising water and/or at least one organic solvent.

Examples of organic solvents include, but are not limited to, linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, such as benzyl alcohol or phenoxyethanol, and mixtures thereof.

Such organic solvent(s) may be present in proportions ranging from 1% to 40% by weight, for example, from 5% to 30% by weight relative to the total weight of each composition in which they are contained.

In at least one embodiment, compositions (A) and (B) comprise water. For example, each of the compositions (A) and (B) comprises at least 5% by weight of water, such as at least 10% by weight of water, or at least 20% by weight of water relative to its total weight.

Compositions (A) and/or (B) according to the present disclosure may also comprise at least one adjuvant, chosen from those conventionally used in compositions for dyeing and/or bleaching keratin fibers, such as conditioning polymers, for example, cationic conditioning polymers; mineral thickeners, and fillers such as clays or talc; organic thickeners, anionic, cationic and nonionic polymeric associative thickeners; antioxidants; penetrants; sequestrants other than those of formula (I) above; fragrances; dispersants; film-forming agents; ceramides; preserving agents; or opacifiers.

The adjuvant(s) may be present in an amount for each of them ranging from 0.01% to 20% by weight relative to the weight of each composition.

In at least one embodiment, composition (A) is in the form of an oil-in-water emulsion (known as a direct emulsion) or a water-in-oil emulsion (known as an inverse emulsion).

The present disclosure also relates to a process for dyeing and/or bleaching keratin fibers, comprising applying to the fibers the agent as described above.

In at least one embodiment, the agent applied to the keratin fibers results from the mixing of compositions (A) and (B), this mixing being performed either before application to the keratin fibers (extemporaneous preparation) or directly on the keratin fibers (successive application to the fibers of compositions (A) and (B) without intermediate rinsing).

In at least one embodiment, the process according to the disclosure comprises applying compositions (A), and then (B) successively and without intermediate rinsing to wet or dry fibers.

In at least one embodiment, the process according to the disclosure comprises, mixing extemporaneously compositions (A) and (B) to form an agent, and applying the agent to wet or dry keratin fibers. In this case, the time between the mixing of compositions (A) and (B) and the application of the mixture to the hair does not exceed, for example, 30 minutes, such as 10 minutes, or 5 minutes.

The weight ratio of the amount of composition (A) used to the amount of composition (B) used may range from 0.2 to 3 and for example from 0.3 to 1.

In addition, the mixture present on the fibers (resulting either from the extemporaneous mixing of compositions (A) and (B), or from the successive application of these compositions) is left in place for a period of time, for example, ranging from about 1 minute to 1 hour, such as from 5 minutes to 30 minutes.

The temperature during the process can range from room temperature (e.g. from 15 to 25° C.) to 80° C., for example, from room temperature to 60° C.

After the treatment, the human keratin fibers are optionally rinsed with water, optionally washed with a shampoo and then rinsed with water, before being dried or left to dry.

An aspect of the disclosure is directed to a multi-compartment dyeing and/or bleaching device or "kit", formed from a first compartment containing composition (A) and a second compartment containing composition (B), compositions (A) and (B) being as described above.

This device or kit may be equipped with an applicator for dispensing the desired mixture on the hair, such as the devices described in patent FR 2 586 913.

This device may be accompanied by at least one composition for washing and/or conditioning keratin fibers, which is intended to be applied before or after the dyeing and/or bleaching treatment according to the disclosure.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow serve to illustrate embodiments of the present disclosure without, however, being limiting in nature.

EXAMPLE

The following oxidation dye agents were prepared (in the tables below, the amounts are expressed in grams):
Dye Composition (A):

| Composition | A1 | A2 |
|---|---|---|
| Liquid petroleum jelly | 55 | 55 |
| Octyldodecanol | 10 | 10 |
| Distearyldimethylammonium-modified hectorite | 1.5 | 1.5 |
| Propylene carbonate | 0.5 | 0.5 |
| Oleyl alcohol 10 OE | 5 | 5 |
| Propylene glycol | 2 | 2 |
| Ethanol | 2.5 | 2.5 |

-continued

| Composition | A1 | A2 |
|---|---|---|
| Hexylene glycol | 1 | 1 |
| Dipropylene glycol | 1 | 1 |
| Monoethanolamine | 4.5 | 4.5 |
| POE/POP/POE (Poloxamer 184) | 9 | 9 |
| Ascorbic acid | 0.25 | 0.25 |
| Diethylenetriaminepentaacetic acid, pentasodium salt, as an aqueous 40% solution | — | 1.0 |
| para-Phenylenediamine | 0.03 | 0.03 |
| Resorcinol | 0.04 | 0.04 |
| 1-Hydroxy-3-aminobenzene | 0.002 | 0.002 |
| 1-β-Hydroxyethyloxy-2,4-diaminobenzene dihydrochloride | 0.0003 | 0.0003 |
| N,N-Bis(2-hydroxyethyl)-p-phenylenediamine sulfate monohydrate | 0.006 | 0.006 |
| Water | qs 100 | qs 100 |

Composition A2 corresponds to a composition (A) in accordance with the present disclosure, whereas composition A1 is a comparative composition not containing any compound of formula (I).

Oxidizing Composition (B):

| Composition | B |
|---|---|
| Aqueous solution of hydrogen peroxide at 50% by weight | 12 |
| Sodium stannate | 0.04 |
| Tetrasodium pyrophosphate | 0.03 |
| Liquid petroleum jelly | 20 |
| Aqueous solution at 40% by weight of tetramethylhexamethylenediamine/1,3-dichloropropylene or Hexadimethrine chloride | 0.1 |
| Non-stabilized aqueous solution at 40% by weight of polydimethyldiallylammonium chloride or Polyquaternium-6 | 0.2 |
| Glycerol | 0.5 |
| Cetearyl alcohol | 8 |
| Oxyethylenated cetylstearyl alcohol (33 OE) | 3 |
| Oxyethylenated rapeseed acid amide (4 OE) | 1.2 |
| Vitamin E: DL-α-tocopherol | 0.1 |
| Phosphoric acid | qs pH 2.2 |
| Water | qs 100 |

The compositions described above were mixed at the time of use in the following manner:
  10 g of the dye composition A1 was mixed with 10 g of the oxidizing composition B, and
  10 g of the dye composition A2 was mixed with 10 g of the oxidizing composition B, respectively.

The mixture resulting from compositions A2 and B did not show any untimely swelling over time, unlike the mixture of compositions A1 and B.

When applied to the hair, the mixture resulting from compositions A2 and B also gave very uniform dyeing results.

What is claimed is:

1. An agent for dyeing and/or bleaching keratin fibers, consisting of:
  a first composition (A) comprising at least one basifying agent, and
  a second composition (B) comprising at least one oxidizing agent,
  wherein,
  at least one of the two compositions (A) and (B) comprises at least one fatty substance not containing any carboxylic acid functional groups, the total amount of the at least one fatty substance in the mixture of compositions (A) and (B) representing at least 20% by weight relative to the total weight of the mixture, and
  at least one of the compositions (A) and (B) comprises at least one sequestrant chosen from those of formula (I) and acids thereof:

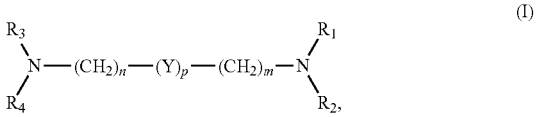

wherein
p is an integer equal to 0 or 1,
n and m are integers, independently of each other, equal to 0, 1 or 2; the sum n+m being equal to at least 1,
$R_1$, $R_2$, $R_3$ and $R_4$ represent, independently of each other, a hydrogen atom, —$CH_2CO_2M1$ or —$CH(CO_2M2)(CH_2CO_2M3)$,
Y represents $NCH_2CO_2M4$,
M1, M2, M3, and M4 denote, independently of each other, a hydrogen atom, cations derived from an alkali metal or an alkaline-earth metal, cations derived from an optionally hydroxylated organic amine, or an ammonium cation,
with the understanding that if p is 0, then $R_1$ and $R_3$ both represent a hydrogen atom, and $R_2$ and $R_4$ both represent, independently of each other, —$CH(CO_2M2)(CH_2CO_2M3)$, and
if p is 1, then n and m are each at least 1.

2. The agent according to claim 1, wherein the at least one basifying agent is chosen from aqueous ammonia, alkali metal carbonates, alkanolamines and derivatives thereof, sodium hydroxide, potassium hydroxide and the compounds of formula (II):

wherein W is a $C_1$-$C_6$ alkylene residue optionally substituted with a hydroxyl group or a $C_1$-$C_6$ alkyl radical; Rx, Ry, Rz and Rt, which may be identical or different, represent a hydrogen or a $C_1$-$C_6$ alkyl, $C_1$-$C_6$ hydroxyalkyl, or $C_1$-$C_6$ aminoalkyl radical.

3. The agent according to claim 2, wherein the at least one basifying agent is chosen from alkanolamines.

4. The agent according to claim 1, wherein the at least one oxidizing agent is chosen from hydrogen peroxide, urea peroxide, alkali metal bromates or ferricyanides, peroxygenated salts, perborates and percarbonates, redox enzymes, optionally in the presence of the respective donor or cofactor thereof.

5. The agent according to claim 4, wherein the at least one oxidizing agent is chosen from alkali metal persulfates, alkaline-earth metal persulfates, laccases, peroxidises, 2-electron oxidoreductases, and hydrogen peroxide.

6. The agent according to claim 1, wherein M1, M2, M3, and M4 are identical, and denote a sodium cation or a potassium cation.

7. The agent according to claim 1, wherein the at least one sequestrant of formula (I) is chosen from:
diethylenetriaminepentaacetic acid (DTPA) and salts thereof, and
ethylenediaminedisuccinic acid (EDDS) and salts thereof.

8. The agent according to claim 7, wherein the salts are alkali metal salts.

9. The agent according to claim 1, wherein the total amount of the at least one sequestrant of formula (I) in acid form in the mixture of the compositions (A) and (B) ranges from 0.001% to 10% by weight relative to the total weight of the mixture.

10. The agent according to claim 9, wherein the total amount of the at least one sequestrant of formula (I) in acid form in the mixture of the compositions (A) and (B) ranges from 0.01% to 5% by weight relative to the total weight of the mixture.

11. The agent according to claim 10, wherein the total amount of the at least one sequestrant of formula (I) in acid form in the mixture of the compositions (A) and (B) ranges from 0.05% to 1% by weight relative to the total weight of the mixture.

12. The agent according to claim 1, wherein the total amount of the at least one fatty substance not containing any carboxylic acid functional groups in the mixture of compositions (A) and (B) represents at least 25% by weight relative to the total weight of the mixture.

13. The agent according to claim 12, wherein the total amount of the at least one fatty substance not containing any carboxylic acid functional groups in the mixture of compositions (A) and (B) represents at least 30% by weight relative to the total weight of the mixture.

14. The agent according to claim 1, wherein the at least one fatty substance not containing any carboxylic acid functional groups is chosen from $C_6$-$C_{16}$ lower alkanes, non-silicone oils of mineral, plant, animal and synthetic origin, fatty alcohols, fatty acid esters, fatty alcohol esters, and non-silicone waxes and silicones.

15. The agent according to claim 14, wherein the at least one fatty substance is chosen from liquid petroleum jelly, polydecenes, liquid esters of fatty acids, and liquid esters of fatty alcohols.

16. The agent according to claim 14, wherein that the at least one fatty substance is liquid petroleum jelly.

17. The agent according to claim 1, wherein the at least one fatty substance not containing any carboxylic acid functional groups is chosen from compounds that are liquid at a temperature of 25° C. and at atmospheric pressure.

18. The agent according to claim 1, wherein composition (A) further comprises at least one oxidation dye chosen from oxidation bases, optionally combined with at least one coupler, and/or at least one direct dye.

19. The agent according to claim 1, wherein compositions (A) and (B) comprise direct dyes or any oxidation dyes not exceeding 0.005% by weight relative to the total weight of each composition.

20. The agent according to claim 19, wherein compositions (A) and (B) do not comprise any direct dyes or any oxidation dyes.

21. The agent according to claim 1, wherein composition (A) is in the form of an oil-in-water emulsion or a water-in-oil emulsion.

22. A process for dyeing and/or bleaching keratin fibers, comprising
applying composition (A) comprising at least one basifying agent, and
applying composition (B) comprising at least one oxidizing agent successively and without intermediate rinsing to wet or dry fibers,
wherein,
at least one of the compositions (A) and (B) comprises at least one fatty substance not containing any carboxylic acid functional groups, the total amount of the at least one fatty substance in the mixture of compositions (A) and (B) representing at least 20% by weight relative to the total weight of the mixture, and
at least one of the compositions (A) and (B) comprising at least one sequestrant chosen from those of formula (I) and acids thereof:

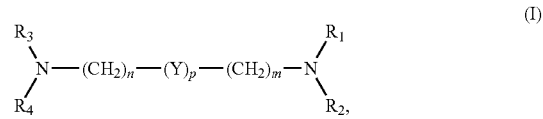

wherein
p is an integer equal to 0 or 1,
n and m are integers, independently of each other, equal to 0, 1 or 2; the sum n+m being equal to at least 1,
$R_1$, $R_2$, $R_3$ and $R_4$ represent, independently of each other, a hydrogen atom, —$CH_2CO_2M1$ or —$CH(CO_2M2)(CH_2CO_2M3)$,
Y represents $NCH_2CO_2M4$,
M1, M2, M3, and M4 denote, independently of each other, a hydrogen atom, cations derived from an alkali metal or an alkaline-earth metal, cations derived from an optionally hydroxylated organic amine, or ammonium cation,
with the understanding that if p is 0, then $R_1$ and $R_3$ both represent a hydrogen atom, and $R_2$ and $R_4$ both represent, independently of each other, —$CH(CO_2M2)(CH_2CO_2M3)$, and
if p is 1, then n and m are each at least 1.

23. A process for dyeing and/or bleaching keratin fibres, comprising the application of the agent as defined in any one of claims 1 to 21, by
mixing extemporaneously
composition (A) comprising at least one basifying agent, and
composition (B) comprising at least one oxidizing agent
to form a mixture,
wherein
at least one of the compositions (A) and (B) comprises at least one fatty substance not containing any carboxylic acid functional groups, the total amount of the fatty substance in the mixture of compositions (A) and (B) representing at least 20% by weight relative to the total weight of the mixture, and
at least one of the compositions (A) and (B) comprises at least one sequestrant chosen from those of formula (I) and acids thereof:

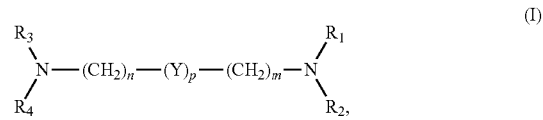

wherein
p is an integer equal to 0 or 1,
n and m are integers, independently of each other, equal to 0, 1 or 2; the sum n+m being equal to at least 1,
$R_1$, $R_2$, $R_3$ and $R_4$ represent, independently of each other, a hydrogen atom, —$CH_2CO_2M1$ or —$CH(CO_2M2)(CH_2CO_2M3)$,
Y represents $NCH_2CO_2M4$,
M1, M2, M3, and M4 denote, independently of each other, a hydrogen atom, cations derived from an alkali metal or an alkaline-earth metal, cations derived from an optionally hydroxylated organic amine, or ammonium cation,
with the understanding that if p is 0, then $R_1$ and $R_3$ both represent a hydrogen atom, and $R_2$ and $R_4$ both represent, independently of each other, —$CH(CO_2M2)(CH_2CO_2M3)$, and
providing that, if p is 1, then n and m are each at least 1,
and,
applying the mixture to wet or dry fibers.

24. A multi-compartment dyeing and/or bleaching device or kit, formed from a first compartment containing a composition (A) comprising at least one basifying agent, and at a second compartment containing a composition (B) comprising at least one oxidizing agent, wherein,
at least one of the compositions (A) and (B) comprises at least one fatty substance not containing any carboxylic acid functional groups, the total amount of the fatty substance in the mixture of compositions (A) and (B) representing at least 20% by weight relative to the total weight of the mixture, and
at least one of the compositions (A) and (B) comprises at least one sequestrant chosen from those of formula (I) and acids thereof:

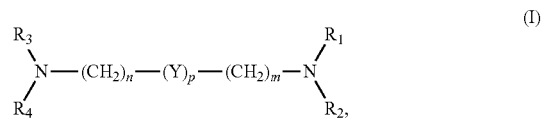

wherein
p is an integer equal to 0 or 1,
n and m are integers, independently of each other, equal to 0, 1 or 2; the sum n+m being equal to at least 1,
$R_1$, $R_2$, $R_3$ and $R_4$ represent, independently of each other, a hydrogen atom, —$CH_2CO_2M1$ or —$CH(CO_2M2)(CH_2CO_2M3)$,
Y represents $NCH_2CO_2M4$,
M1, M2, M3, and M4 denote, independently of each other, a hydrogen atom, cations derived from an alkali metal or an alkaline-earth metal, cations derived from an optionally hydroxylated organic amine, or ammonium cation,
with the understanding that if p is 0, then $R_1$ and $R_3$ both represent a hydrogen atom, and $R_2$ and $R_4$ both represent, independently of each other, —$CH(CO_2M2)(CH_2CO_2M3)$, and
and, if p is 1, then n and m are each at least 1.

* * * * *